United States Patent [19]

Tomita et al.

[11] Patent Number: 5,729,349
[45] Date of Patent: Mar. 17, 1998

[54] METHOD AND DEVICE FOR DETERMINING FIBER ORIENTATION OF PAPER, AND APPARATUS FOR REMOVING IMAGE FORMING SUBSTANCE FROM PAPER

[75] Inventors: Kan Tomita; Nobuo Sakuma, both of Tokyo; Takashi Mama, Yokohama, all of Japan

[73] Assignee: Ricoh Company, Ltd., Tokyo, Japan

[21] Appl. No.: 596,860

[22] Filed: Feb. 9, 1996

[30] Foreign Application Priority Data

Feb. 10, 1995 [JP] Japan .................. 7-022705

[51] Int. Cl.⁶ .................. G01N 21/86; G03G 21/00
[52] U.S. Cl. .................. 356/429; 250/559.16; 356/446; 162/4
[58] Field of Search .................. 356/429, 446; 250/559.15, 559.16, 559.18; 162/4

[56] References Cited

U.S. PATENT DOCUMENTS

| | | | |
|---|---|---|---|
| T932,008 | 3/1975 | Davis et al. | 250/571 |
| 3,807,868 | 4/1974 | Simula | 356/429 |
| 4,606,645 | 8/1986 | Matthews et al. | 356/446 |
| 5,006,189 | 4/1991 | Tsukamoto et al. | |
| 5,353,108 | 10/1994 | Tsukamoto . | |
| 5,474,617 | 12/1995 | Saito et al. . | |
| 5,475,233 | 12/1995 | Fukuoka et al. | 250/559.1 |
| 5,542,985 | 8/1996 | Machida et al. | 134/38 |
| 5,547,793 | 8/1996 | Kuramoto et al. | 430/97 |
| 5,640,244 | 6/1997 | Hellstrom et al. | 356/429 |

FOREIGN PATENT DOCUMENTS

| | | |
|---|---|---|
| 60-230899 | 11/1985 | Japan . |
| 1-297294 | 11/1989 | Japan . |
| 2-55195 | 2/1990 | Japan . |
| 3-68460 | 7/1991 | Japan . |
| 4-64472 | 2/1992 | Japan . |
| 4-64473 | 2/1992 | Japan . |
| 4-67043 | 3/1992 | Japan . |
| 4-82983 | 3/1992 | Japan . |
| 4-89271 | 3/1992 | Japan . |
| 4-94958 | 3/1992 | Japan . |
| 4-333088 | 11/1992 | Japan . |
| 5-173454 | 7/1993 | Japan . |
| 5-216374 | 8/1993 | Japan . |

*Primary Examiner*—Richard A. Rosenberger
*Attorney, Agent, or Firm*—Oblon, Spivak, McClelland, Maier & Neustadt, P.C.

[57] ABSTRACT

In an image forming apparatus, a device for removing an image forming substance from a paper or similar image holding medium senses the orientation of fibers constituting the paper. While a light beam is emitted obliquely toward the paper, the diffused distribution distribution of the resulting reflection is measured in order to determine the orientation of the fibers. A preselected relation is set up between the fibers and the direction of paper transport on the basis of the determined orientation. Further, a condition for applying an unstabilizing liquid to the paper and a condition for drying the paper are varied on the basis of the determined orientation.

10 Claims, 12 Drawing Sheets

METHOD AND DEVICE FOR DETERMINING FIBER ORIENTATION OF PAPER, AND APPARATUS FOR REMOVING IMAGE FORMING SUBSTANCE FROM PAPER

BACKGROUND OF THE INVENTION

The present invention relates to a method and a device for determining the fiber orientation of a paper accurately, and an apparatus for removing an image forming substance deposited on an image holding medium by a printer or similar image forming apparatus.

Generally, fibers constituting a paper are provided with a certain orientation during the course of production. Let this orientation be referred to as a fiber orientation hereinafter. The paper with a fiber orientation is apt to expand or contact or even curl due to humidity. Therefore, the prerequisite with a copier, printer or similar image forming apparatus dealing with this kind of papers is that the fiber orientation be determined beforehand in order to obviate the above deformation.

Although some papers of fine quality have their fiber orientations printed on packages, many of ordinary papers do not. Even the fine papers cannot have their orientations identified, once they are produced from the packages. It has been customary to determine the fiber orientation of a paper by tearing the paper to see how it tears, or by causing the paper to bend due to its own weight and measuring the amount of bend.

However, the tearing scheme damages and thereby wastes the paper. The bending scheme is not practicable without measuring the amounts of bend in two different directions and then calculating a difference between them. This results in a complicated sensing device, and moreover prevents the measurement from being effected during the course of paper transport in, e.g., a copier because the absolute values noticeably vary due to humidity.

A recent achievement in the image forming art is a method and an apparatus for recycling image holding media on which a toner or similar image forming substance has been deposited by, e.g., a copier. This kind of method and apparatus apply a liquid to the image holding medium and then removes the image forming substance from the medium. Japanese Patent Laid-Open Publication No. 4-255916, for example, discloses a method capable of removing only the image forming substance from the medium without noticeably damaging the texture of the medium. The method disclosed in this document applies to the medium an unstabilizing liquid for unstabilizing the adhesion between the image forming substance and the surface of the medium. The unstabilizing liquid is water, an aqueous solution containing one of a surfactant and a water-soluble polymer, or an aqueous solution containing both of them. The image forming substance is adhered to a separating member by heat or pressure and removed from the medium thereby. In this prior art method, after image forming substance has been removed by the wetted medium, the medium is dried by heat to be recycled. This brings about a problem that the medium is apt to crease during the course of drying or to tear during the course of removal of the image forming substance. The crease and tear of the medium is likely to jam a transport path defined in the apparatus. Moreover, the removal of the image forming substance is deteriorated, and defective image transfer occurs when the recycled medium is reused, depending on the liquid applying condition and drying condition.

A series of researches and experiments showed that the creasing and tearing of the image holding medium are dependent on the fiber orientation and thickness of the medium. For example, the creasing and tearing are apt to occur when the fiber orientation and the direction of medium transport in the apparatus are parallel to each other, and such an occurrence varies in accordance with the liquid applying condition and drying condition. Further, when the medium is relatively thin, it is excessively wetted even when the liquid is applied in the same condition. As a result, the medium looses its flexibility and creases or jams the path. In addition, it is likely that the medium is excessively dried despite the same drying condition and causes defective image transfer to occur when reused for image formation. When the medium is relatively thick, the amount of liquid application is apt to be short despite the same liquid applying condition, thereby deteriorating the removal of the image forming substance. Also, the drying is apt to be short despite the same drying condition, so that the medium is likely to crease or jam the transport path when reused for image formation.

SUMMARY OF THE INVENTION

It is therefore an object of the present invention to provide a method and a device capable of determining the fiber orientation of an image holding medium without destroying or contacting the medium.

It is another object of the present invention to provide an apparatus capable of determining the fiber orientation of an image holding medium, setting up a preselected relation between the fiber orientation and the direction of medium transport on the basis of the fiber orientation, and thereby freeing the medium from creases.

It is still another object of the present invention to provide an apparatus capable of determining the fiber orientation of an image holding medium, varying a liquid applying condition and a drying condition on the basis of the fiber orientation, and thereby insuring the expected removal of an image forming substance without lowering a processing speed while freeing the medium from creasing and tearing and from defective image transfer at the time of reuse.

It is a further object of the present invention to provide an apparatus capable of determining the thickness of an image holding medium, varying a liquid applying condition and a drying condition on the basis of the thickness, and thereby insuring the expected removal of an image forming substance without lowering a processing speed while freeing the medium from creasing and tearing and from defective image transfer at the time of reuse.

In accordance with the present invention, a method of determining the orientation of fibers constituting a paper has the steps of emitting a light beam obliquely toward the paper, and measuring a diffused reflection distribution of a resulting reflection from the paper.

In accordance with the present invention, a method of determining the orientation of fibers constituting a paper has the steps of emitting a light beam obliquely toward the paper, and measuring quantities of light at at least two points in a diffused reflection distribution of the resulting reflection.

In accordance with the present invention, a method of determining the orientation of fibers constituting a paper has the steps of emitting light beams obliquely toward the paper in at least two directions perpendicular to each other, measuring quantities of light at at least two points in each of the resulting diffused reflection distributions to thereby determine the orientation, and totally determining the orientation on the basis of the results of the above determination.

In accordance with the present invention, a device for determining the orientation of fibers constituting a paper has a light emitting unit for emitting a light beam obliquely toward the paper, and a light quantity measuring unit for measuring quantities of light at at least two points in the resulting diffused reflection distribution. The light emitting unit and light quantity measuring unit are constructed integrally with each other.

In accordance with the present invention, an apparatus for removing an image forming substance from fibers constituting the surface of an image holding medium has a first medium stacking unit for stacking the image holding medium. A liquid applying unit applies to the image holding medium an unstabilizing liquid which unstabilizes adhesion between the image forming substance and the image holding medium. A fiber orientation sensing unit senses the orientation of the fibers of the image holding medium conveyed from the first medium stacking unit. A determining unit determines, based on the orientation sensed by the fiber orientation sensing unit, whether or not the image holding medium can be subjected to the removal of the image forming substance and including the application of the unstabilizing liquid. A rotating mechanism rotates the image holding medium which cannot be subjected to the removal of the image forming substance, as determined by the determining unit, such that the image holding medium is reoriented substantially 90 degrees with respect to the intended direction of medium transport.

In accordance with the present invention, an apparatus for removing an image forming substance from fibers constituting the surface of an image holding medium has a liquid applying unit for applying to the image holding medium an unstabilizing liquid which unstabilizes adhesion between the image forming substance and the image holding medium. A separating unit separates the image forming substance from the image holding medium to which the unstabilizing liquid has been applied. A drying unit dries the image holding medium from which the image forming substance has been removed. A fiber orientation sensing unit senses the orientation of the fibers of the image holding medium. A controller varies the drying condition of the drying unit on the basis of the sensed orientation.

In accordance with the present invention, an apparatus for removing an image forming substance from fibers constituting the surface of an image holding medium has a liquid applying unit for applying to the image holding medium an unstabilizing liquid which unstabilizes adhesion between the image forming substance and the image holding medium. A fiber orientation sensing unit senses the orientation of the fibers of the image holding medium. A controller varies the liquid applying condition of the liquid applying unit on the basis of the orientation sensed.

In accordance with the present invention, an apparatus for removing an image forming substance from fibers constituting the surface of an image holding medium has a liquid applying unit for applying to the image holding medium an unstabilizing liquid which unstabilizes adhesion between the image forming substance and the image holding medium. A separating unit separats the image forming substance from the image holding medium to which the unstabilizing liquid has been applied. A drying unit dries the image holding medium from which the image forming substance has been removed. A thickness sensor senses the thickness of the image holding medium. A controller varies the drying condition of the drying unit on the basis of the thickness sensed.

In accordance with the present invention, an apparatus for removing an image forming substance from fibers constituting the surface of an image holding medium has a liquid applying unit for applying to the image holding medium an unstabilizing liquid which unstabilizes adhesion between the image forming substance and the image holding medium. A thickness sensor senses the thickness of the image holding medium. A controller varies the liquid applying condition of the liquid applying unit on the basis of the thickness sensed.

BRIEF DESCRIPTION OF THE DRAWINGS

The above and other objects, features and advantages of the present invention will become more apparent from the following detailed description taken with the accompanying drawings in which.

DESCRIPTION OF THE PREFERRED EMBODIMENTS

Preferred embodiments of the method, device and apparatus in accordance with the present invention will be described hereinafter.

1st Embodiment

Figure 1:
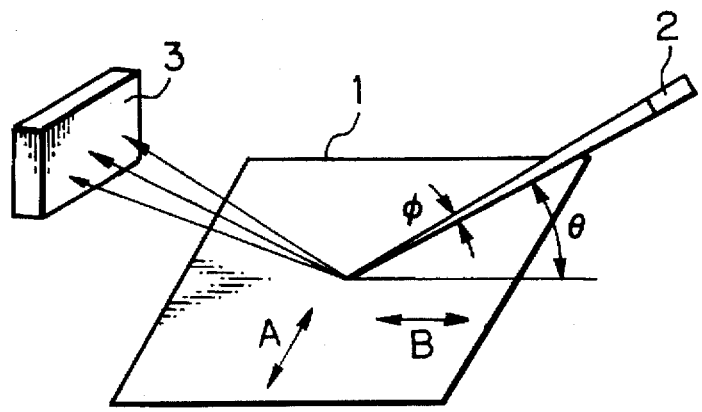
FIG. 1 is a perspective view of a first embodiment of the fiber orientation determining device in accordance with the present invention.

Referring to FIG. 1 of the drawings, a device for determining the fiber orientation of a paper and representative of a first embodiment of the present invention is shown. As shown, the apparatus has a light emitting unit or light emitting means 2 and a light sensing unit or light quantity measuring means 3. While the light emitting unit 2 emits a light beam obliquely toward a paper 1, a diffused reflection distribution of the reflection from the paper 1 is incident to the light sensing unit 3. The unit 2 may be implemented by, e.g., a lamp or light source and optical members including a lens and mirrors. The unit 3 may be implemented by an image pick-up tube or a CCD (Charge Coupled Device) image sensor or similar solid-state imaging device. The beam issuing from the unit 2 has a substantially circular cross-section and has a diameter φ of less than about 10 mm inclusive, preferably 4 mm to 8 mm, as measured at a position just before the paper 1. The beam obliquely incident to the paper 1 forms an oblong spot on the paper 1. So long as the angle of incidence θ of the beam to the the paper 1 is less than 70 degrees inclusive, the diffused reflection distribution can be measured. However, the angle θ should preferably range from about 10 degrees to about 40 degrees because such a range causes the distribution to noticeably change in accordance with the kind of the paper and the fiber orientation.

Figure 2A:
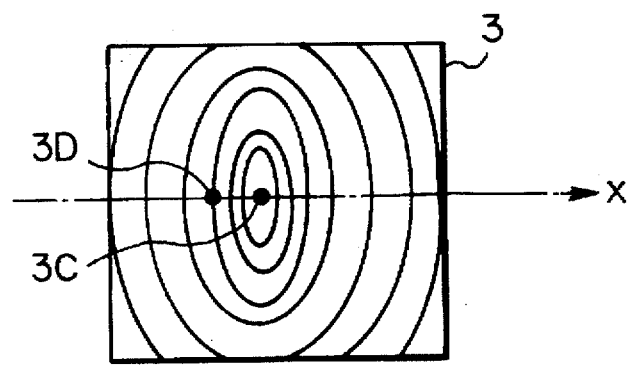
FIG. 2A shows the diffused reflection distribution of a reflection from a paper in the first embodiment.
Figure 2B:
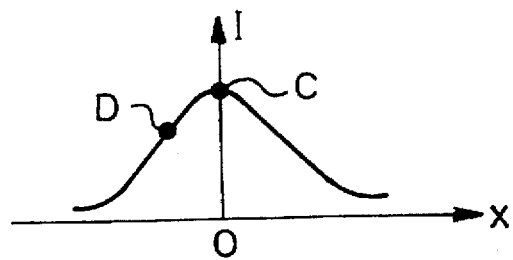
FIG. 2B shows the diffused reflection distribution of a reflection in a direction x shown in FIG. 2A.
Figure 3A:
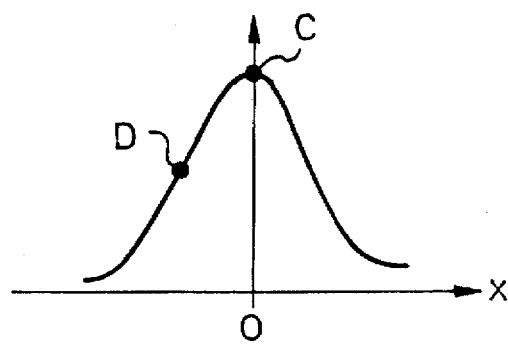
FIG. 3A shows the diffused reflection distribution of the reflection in the direction x and appearing when the fiber orientation of a paper is A.
Figure 3B:
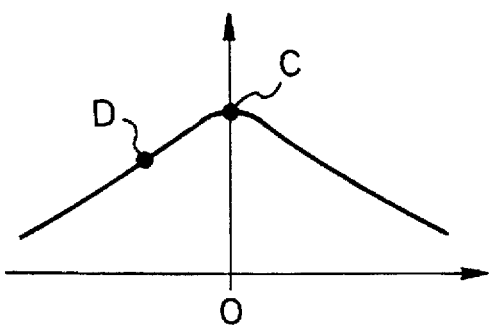
FIG. 3B shows the diffused reflection distribution of the reflection in the direction x and appearing when the fiber orientation of a paper is B.

FIG. 2A shows contour lines representative of the intensities of reflection as measured on the light-sensitive surface of the light sensing unit 3. FIG. 2B shows a diffused reflection distribution I as measured on a line extending along a dash-and-dot line shown in FIG. 2A, i.e., the direction substantially perpendicular to the plane containing the optical axis of the incident light and that of the reflection (referred to as an optical axis plane hereinafter). Because the fibers constituting the paper 1 are oriented in substantially the same direction, they serve in the same manner as a diffraction grating in response to the incident beam. Therefore, the diffused reflection distribution I of the reflection changes on the basis of the fiber orientation of the paper 1 relative to the optical axis plane. For example, when the fiber orientation of the paper 1 is A shown in FIG. 1, the distribution I concentrates at the center of the optical axis plane, as shown in FIG. 3A. When the fiber orientation is B also shown in FIG. 1, the distribution I is small at the center of the optical axis plane and spread in the direction perpendicular to the plane, as shown in FIG. 3B. In FIGS. 3A and 3B, reflection intensities C and D are respectively measured at points C and D shown in FIG. 2A.

As stated above, the illustrative embodiment emits a light beam obliquely toward the paper 1 and measures the diffused reflection distribution of the reflection from the paper 1, thereby determining the fiber orientation of the paper 1. With this scheme, the embodiment does not damage the paper 1. Moreover, because the embodiment determines the fiber orientation without contacting the paper 1, it is scarcely susceptible to humidity and other environmental conditions. Hence, the embodiment is capable of determining the orientation more accurately than the conventional scheme which determines it on the basis of the tear or the warp of a paper.

The single light receiving unit 3 may be replaced with two light-sensitive elements 3C and 3D respectively located at a point C substantially on the optical axis of FIG. 2A and a point D slightly spaced from the optical axis. The light-sensitive elements 3C and 3D may be implemented by PIN photosensors, phototransistors or the like. The reflection intensities measured by the elements 3C and 3D correspond to the intensities C and D of FIGS. 3A and 3B and vary on the basis of the fiber direction. Hence, this also successfully determines the fiber orientation. For the determination, use may be made of the following relation:

(output of element 3C)/(output of element 3D)>desired number
(selected in matching relation to positions of elements 3C and 3D)

By determining the fiber orientation on the basis of the ratio between the reflection intensities measured at the two points, it is possible to obviate the influence of the light distribution of the light emitting element 2 and the reflectance of the paper 1.

Figure 4:
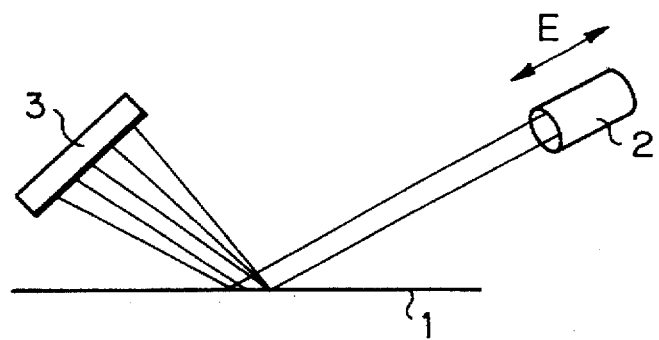
FIG. 4 shows how the first embodiment determines the fiber orientation by use of a parallel light.
Figure 5A:
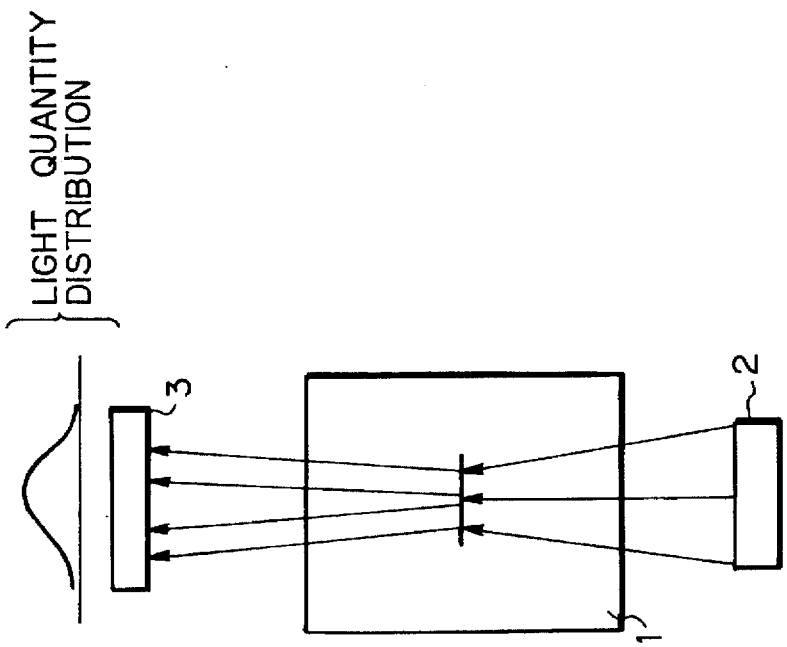
FIGS. 5A–5C respectively demonstrate how the first embodiment determines the fiber orientation by use of a parallel light, diffused light, and convergent light.
Figure 5B:
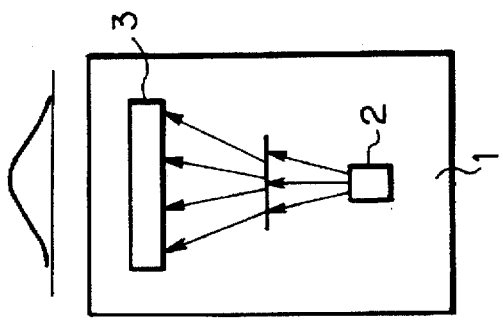
Figure 5C:
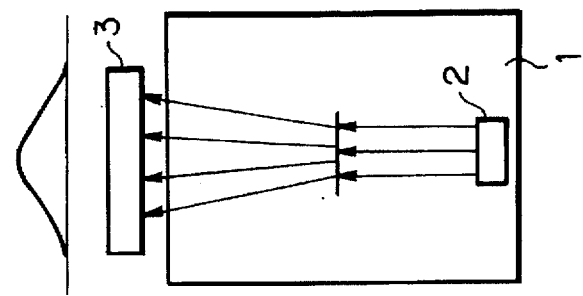

As shown in FIG. 4, the light beam issuing from the light emitting unit 2 may be replaced with a parallel light as viewed in the optical axis plane. In this case, even if the unit 2 is displaced in a direction E, the intensity of light incident to the paper 1 changes little. This reduces changes in the diffused reflection distribution of the reflection from the paper 1. FIG. 5A shows the parallel light issuing from the light emitting unit 2 toward the paper 1 in a plane perpendicular to the optical axis plane. As shown in FIG. 5B, when use is made of a diffused light, it is possible to reduce the distance between the units 2 and 3 and to thereby make the arrangement compact. As shown in FIG. 5C, when use is made of a convergent light, the distance between the units 2 and 3 can be increased in order to enhance free layout. FIGS.

6A–6C show a condition wherein the units 2 and 3 are so arranged as to provide the light with substantially the same diameter on the paper 1 and on the light-sensitive surface of the unit 3.

If desired, the above units 2 and 3 or their modifications may be arranged in two pairs perpendicularly to each other with respect to the paper 1. Then, the diffused reflection distribution can be measured in two directions at the same time, i.e., the direction substantially parallel to the fiber orientation of the paper 1 and the direction substantially perpendicular to the same. By comparing the difference between the two distributions, it is possible to determine the fiber orientation with accuracy even if the distribution varies due to a difference in the kind of the paper.

Figure 6A:
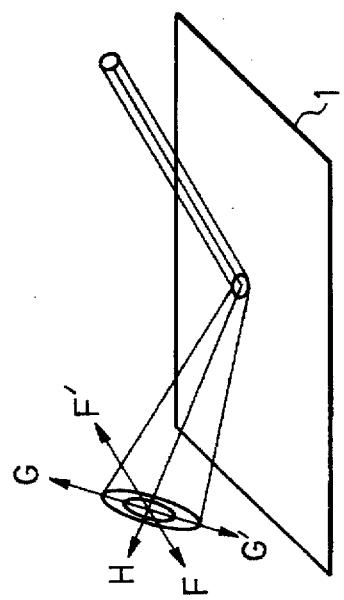
FIG. 6A shows a diffused reflection from a paper in the first embodiment.
Figure 6B:
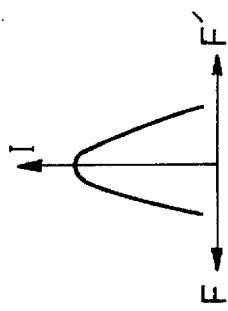
FIGS. 6B and 6C respectively show diffused reflection distributions of reflections in directions FF' and GG' shown in FIG. 6A.
Figure 6C:
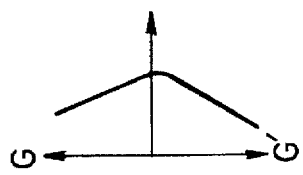

When the beam issuing from the unit 2 has a substantially circular cross-section, as shown in FIG. 6A, it forms an oblong spot on the paper 1. As a result, the reflection incident to the light-sensitive surface of the unit 3 forms a vertically long diffused reflection distribution, as shown in FIG. 2A; that is, the diffused reflection distributions in directions FF' and GG' shown in FIG. 6A appear as shown in FIGS. 6B and 6C, respectively. Hence, when at least two light-sensitive elements are located in the diffused reflection distribution, as shown in FIG. 4, it is preferable that they be arranged in the direction FF' which is substantially perpendicular to the optical axis plane. This will amplify the change in diffused reflection intensity due to the difference in fiber orientation and will thereby promote easy determination.

Figure 7A:
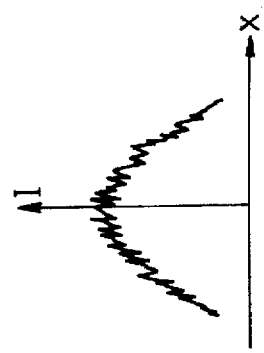
FIGS. 7A and 7B respectively show a spatial distribution particular to a case wherein the sensed light intensities are not integrated and a case wherein they are integrated.
Figure 7B:
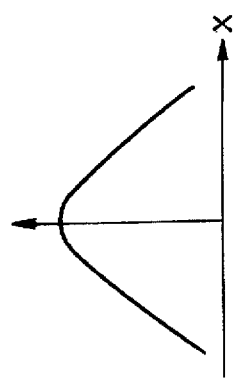

If the surface of the paper 1 is rough, the diffused reflection distribution as measured on the light-sensitive surface of the unit 3 will contain much noise, as shown in FIG. 7A. In light of this, while the distance between the the unit 2 and the incident point of the paper 1 and the distance between the unit 3 and the incident point are maintained constant, the paper 1 may be moved in the horizontal direction. In this case, a measuring system will be so configured as to integrate reflection intensities. This successfully reduces the noise level of the distribution, as shown in FIG. 7B.

Figure 8A:
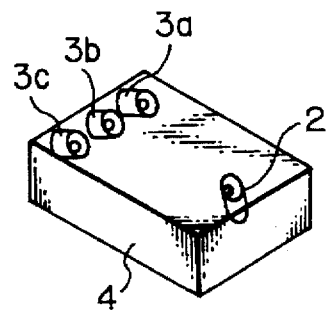
FIG. 8A is a perspective view of optical sensing means representative of a modification of the first embodiment.
Figure 8B:
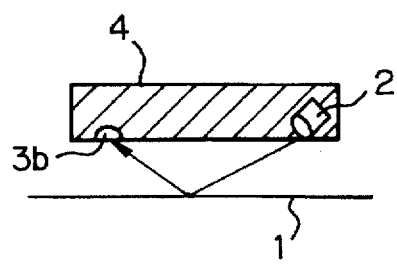
FIG. 8B is a section of the modification shown in FIG. 8A.
Figure 8C:
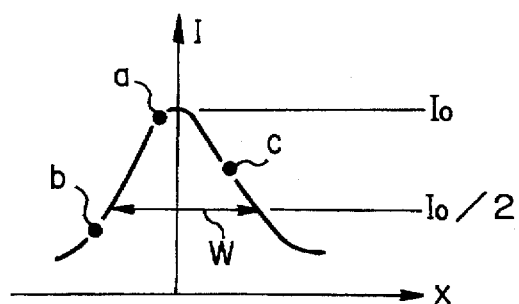
FIG. 8C shows the diffused reflection distribution particular to the modification of FIG. 8A.

As shown in FIGS. 8A and 8B, three PIN photosensors $3a$, $3b$ and $3c$ playing the role of the unit 3 may be combined with the unit 2 so as to implement a compact sensing device 4. With this configuration, it is possible to determine a fiber orientation by estimating a diffused reflection distribution by use of the outputs (a–c shown in FIG. 8C) of the photosensors $3a$–$3c$ and a suitable approximation equation ($Y=\alpha e-\beta e$ in this specific case), and then producing the width W of a level which is one half of the peak level. If desired, a ratio between such widths W in two different directions may be used. Further, so long as the optical axis of the light incident to the paper 1 and that of the light reflected by the paper 1 are coincident, a fiber orientation may be determined on the basis of a ratio between two of the sensor outputs a–c or a ratio between the sensor output $\alpha$ and (b+c)/2. This scheme insures accurate determination even if the above two optical axes are deviated from each other.

For the unit 2, use may be made of a laser diode or similar laser beam source capable of emitting a coherent light. Although a coherent light produces speckles on the surface of the unit 3 and thereby introduces noise in the diffused reflection distribution, the accurate determination of a fiber orientation is enhanced because the difference ascribable to the fiber orientation in the distribution increases.

2nd Embodiment

Figure 9:
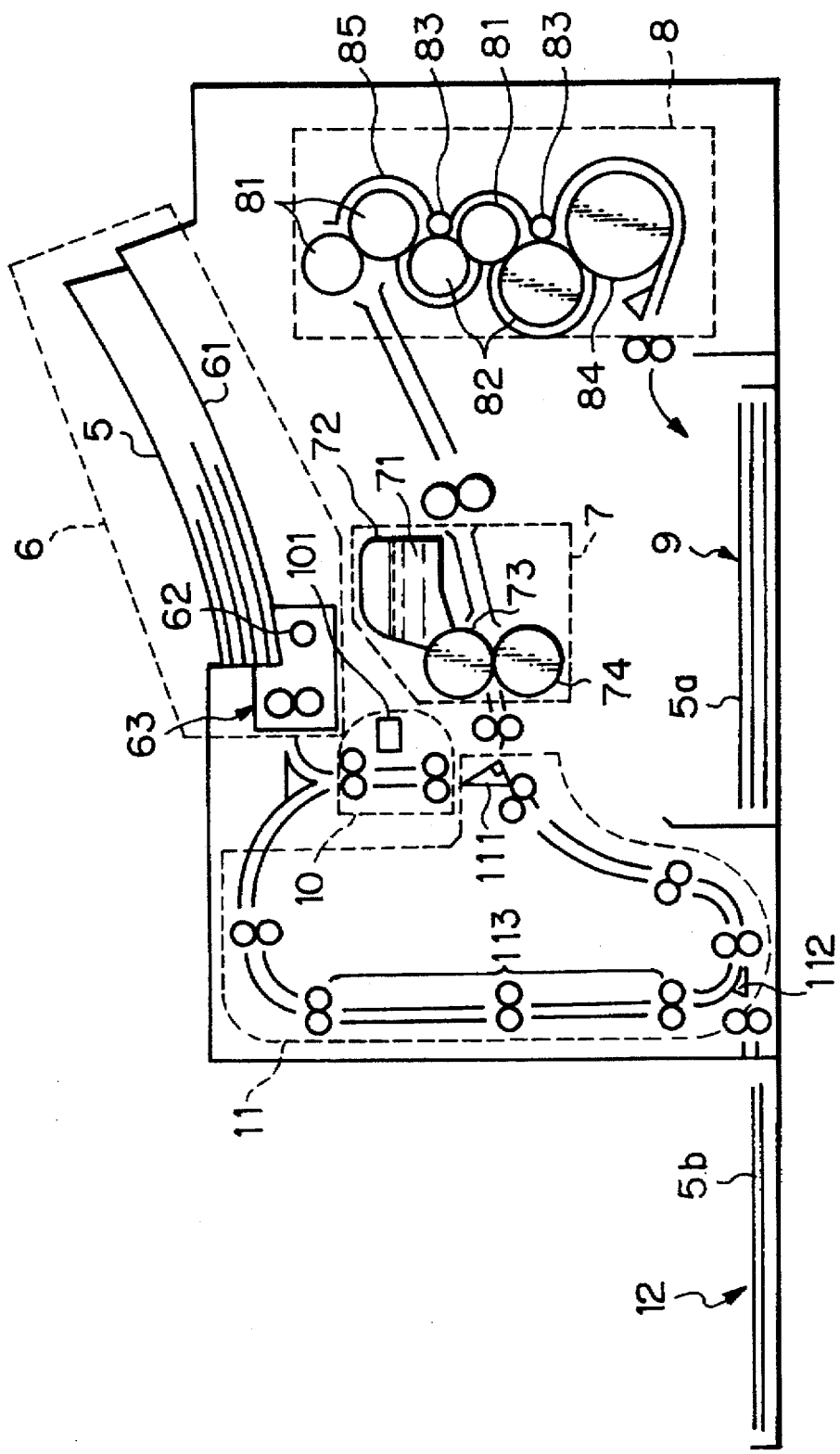
FIG. 9 is a front view of an apparatus for removing an image forming substance from an image holding medium and representative of a second embodiment of the present invention.

FIG. 9 an apparatus for removing an image forming substance from an image holding medium and representative of a second embodiment of the present invention. The apparatus is constructed to remove a thermally meltable toner, or image forming substance, deposited on an image holding medium or paper by an image transfer type electrophotographic copier. As shown, the apparatus has a paper feeding unit or first medium stacking means 6 loaded with a stack of papers 5 carrying toner images thereon, and for feeding the papers 5 one by one. A liquid applying unit or liquid applying means 7 applies an unstabilizing liquid to the paper 5 fed from the paper feeding unit 6. A toner separating and paper drying unit 8 removes the toner from the paper 5 come out of the unit 7 and then dries the paper 5. A receiver unit 9 receives the paper 5 coming out of the unit 8.

Specifically, the paper feeding unit 6 has a table 61 on which the papers 5 are stacked face down (image surfaces facing downward). A pick-up roller 62 sequentially feeds the bottom paper 5 to the top paper 5 one at a time. A separator roller pair 63 separates the bottom paper 5 from the overlying papers 5. The specific construction and operation of the paper feeding unit 6 will not be described in detail because they are conventional with an electrophotographic copier.

The liquid applying unit 7 has a vessel 72 storing an unstabilizing liquid 71 to be applied to the paper 5. The liquid 71 may be water or an aqueous solution containing a surfactant for enhancing infiltration, or a solvent. An applicator roller 73 is held in contact with the liquid 71 and rotatable to apply the liquid 71 to the image surface of the paper 5. A back-up roller 74 faces the applicator roller 73 with the intermediary of a paper transport path. For the applicator roller 73, use may be made of a roller formed of a liquid-retaining material, e.g., hydrophilic porous material or sponge, a roller made of rubber or similar elastic material, or a roller made of metal or similar rigid material.

The toner separating and paper drying unit 8 has a conveyor rollers 81, separator rollers or separating members 82 for separating the toner from the paper 5 by heating it, cleaning rollers 83 for removing the toner adhered to the rollers 82, a drier roller 84 for drying the paper 5 free from the toner by heating it, and guides 85 respectively facing the surfaces of the rollers 81, 82 and 84 for guiding the paper 5. The separator rollers 82 each has its surface formed of a material exerting a greater adhering force on the toner softened by heat than the surface of the paper 5.

The above toner removing apparatus is usually operated as follows. The paper 5 fed from the paper feeding unit 6 is wetted by the liquid 71 of the liquid applying unit 7 and then conveyed to the separating and drying unit 8. In the unit 8, the separator rollers 82 soften the toner of the paper 5 by heating it with the result that the toner adheres to the rollers 82. When the paper 5 is separated from the surface of the rollers 82, the toner comes off the paper 5 and deposits on the rollers 82. Then, the paper 5 is dried by the drier roller 84 and then driven out to the receiver unit 9. By the above procedure, it is possible to remove the toner from the paper 5 without damaging the fibers constituting the paper 5.

The embodiment additionally includes arrangements for freeing the paper 5 from, e.g., creases apt to occur when the relation between the fiber orientation of the paper 5 and the direction of paper transport is inadequate. A fiber orientation sensing unit or sensing means 10 is interposed between the paper feeding unit 6 and the liquid applying unit 7 in order to determine the fiber orientation of the paper 5. Means is provided for determining, based on the output of the sensing means 10, whether or not to execute toner removal. A paper rotating unit or rotating means 11 rotates, if necessary, the paper 5 90 degrees with respect to the direction of paper transport and again conveys it to the sensing unit 10. The papers 5 which cannot be subjected to the toner removal, as will be described, are stacked on a discharge tray 12. The sensing unit 10 includes a sensing device 101 which should preferably be capable of determining a fiber orientation accurately without destroying the texture of the paper or contacting it. For example, the first embodiment using a reflection is advantageously applicable to the sensing device 101.

The above determining means may be implemented by a control section, not shown, installed in the body of the toner removing apparatus for controlling the other units. The control section determines, in response to the output of the sensing unit 10, whether the fiber orientation of the paper 5 is substantially parallel to the direction of paper transport, whether it is substantially perpendicular to the above direction, or whether it is indefinite. If the fiber orientation is substantially perpendicular to the direction of paper transport, the control section determines that the paper 5 can be subjected to toner removable. If the fiber orientation is substantially parallel to the above direction or if it is indefinite, the control section determines that the paper 5 cannot be subjected to toner removal. The rotating unit 11 has path selectors 111 and 112 to be driven by the control section, and a repositioning mechanism 113 for changing the orientation of the paper 5 by substantially 90 degrees with respect to the direction of paper transport. A specific construction of the repositioning mechanism 113 is taught in, e.g., Japanese Patent Laid-Open Publication No. 5-162899.

In operation, the fiber orientation sensing unit 10 senses the fiber orientation of the paper 5 conveyed from the paper feeding unit 6. If the control section determines that the fiber orientation is substantially perpendicular to the direction of paper transport, it causes the paper 5 to be directly transported to the liquid applying unit 7. If the control section determines that the fiber orientation is substantially parallel to the direction of paper transport or is indefinite, it determines that the toner removal should not be executed, moves the path selector 111 in order to switch the transport path, and then causes the paper 5 to be conveyed to the repositioning mechanism 113. The mechanism 13 rotates the paper 5 substantially 90 degrees relative to the direction of paper transport, and again drives it toward the sensing unit 10.

The sensing unit 10 again senses the fiber orientation of the paper 5. If the control section determines, based on the resulting output of the sensing unit 10, that the fiber orientation is substantially perpendicular to the direction of transport, it causes the paper 5 to be transported to the liquid applying unit 7. If the control section again determines that the fiber orientation is not substantially perpendicular to the direction of transport or is indefinite, it moves the path selector 112 to select a path leading to the discharge tray 12. As a result, the paper, labeled 5b, is driven out to the discharge tray 12. When the sensing unit 10 is so arranged as to accurately determine that the fiber orientation is indefinite by a single sensing operation, the control section may move the path selector 112 immediately after the paper 5 has moved away from the sensing unit 10 for the first time. Then, the paper 5b will be immediately driven out to the tray 12.

As stated above, this embodiment rotates, if necessary, the paper 5 90 degrees such that its fiber orientation becomes substantially perpendicular to the direction of paper transport, and then executes toner removal including the application of the liquid 71. Hence, the papers 5a are free from creases even when the operator stacks the papers 5 on the paper feeding unit 6 without being conscious of the fiber orientations of the papers 5. Because the paper 5 does not have to be dried slowly in order to obviate creases, the toner removing operation is not slowed down. In addition, because the papers 5b whose fiber orientations are indefinite are driven out to the discharge tray 12, they can be dealt with independently of the other papers 5a without being creased.

If desired, an arrangement may be made such that the paper feeding unit 6 continuously feeds the papers 5, but its operation is interrupted only when the paper 5 is returned from the rotating unit 11. Then, the toner removing time will be reduced.

Figure 10:
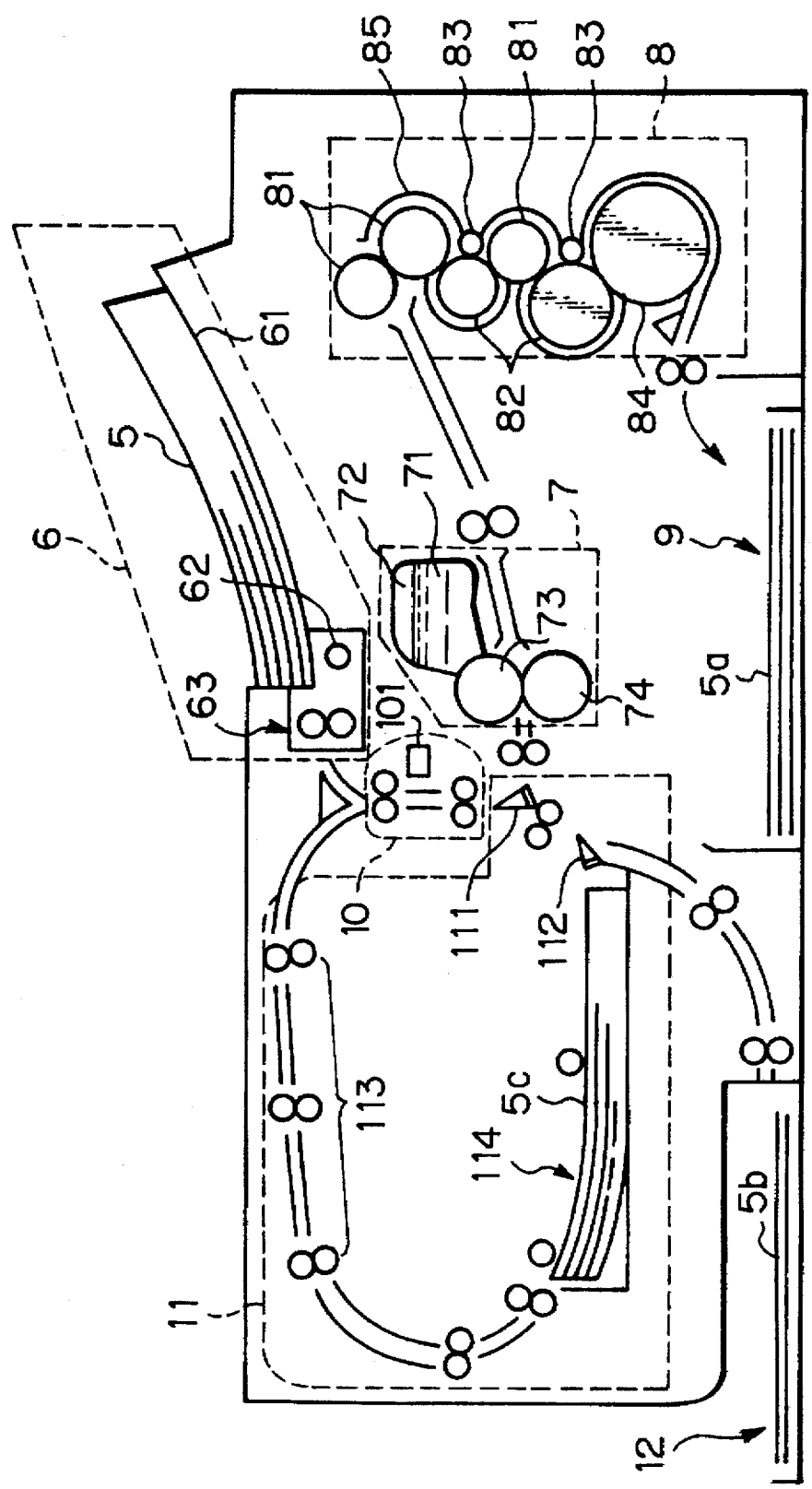
FIG. 10 is a front view showing a modification of the second embodiment.

FIG. 10 shows a modified form of the second embodiment. As shown, the modification includes a refeed tray or second medium stacking means 114 to which the papers, labeled 5c, which cannot be subjected to toner removal are conveyed once. In this case, the paper feeding unit 6 continuously feeds the papers 5 until the papers 5c have been stacked on the tray 114 up to the capacity of the tray 114. When the tray 114 is filled up or when all the papers 5 are fed out from the table 61 of the paper feeding unit 6, the papers 5c are again sequentially transported from the tray 114 to the repositioning mechanism 113. While the tray 114 is shown as being located upstream of the mechanism 113, it may be located downstream of the mechanism 113, if desired.

Figure 11:
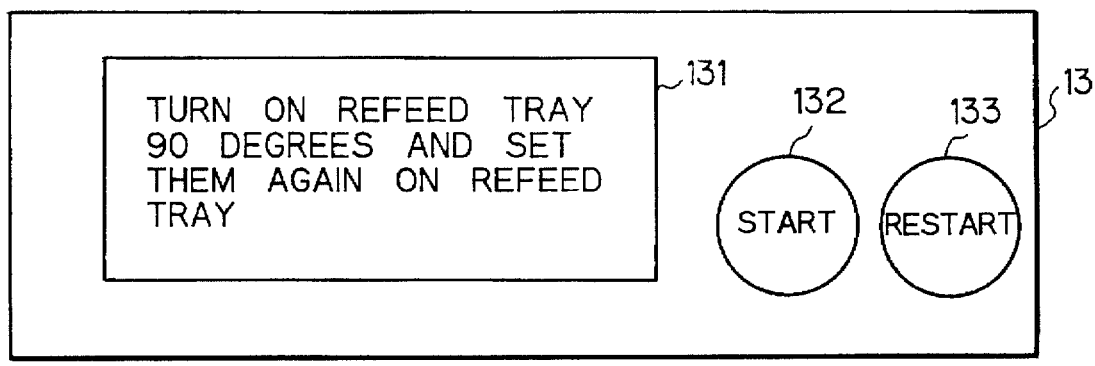
FIG. 11 is a plan view of an operation panel included in the modification shown in FIG. 10.
Figure 12:
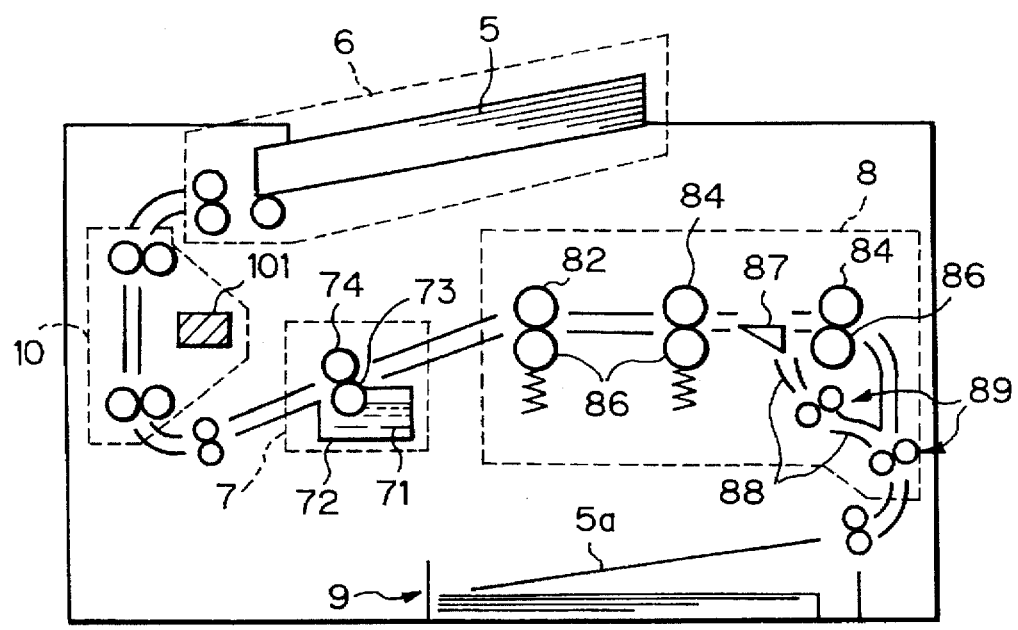
FIG. 12 is a front view of an apparatus for removing an image forming substance from and image holding medium and representative of a third embodiment of the present invention.

As shown in FIG. 12, the paper refeed section between the refeed tray 114 and the sensing unit 10 and including the discharge tray 12, path selector 112 and repositioning mechanism 113 may be omitted. In this modified arrangement, when the tray 114 is filled up or when all the papers 5 are fed out from the table 61, the operator will pick up the paper stack 5c from the tray 114, rotate it substantially 90 degrees with respect to the direction of paper transport, and again sets it on the table 61. This is followed by the same procedure as described in relation to the second embodiment. Assume that the papers 5c are present on the tray 114 after the papers have been fully fed out from the table 61. Then, a visible or audible message for urging the operator to refeed the papers 5 may be produced. FIG. 11 shows a specific message "Turn papers on refeed tray 90 degrees and set them again on tray 90".

Further, as shown in FIG. 11, a refeed button 133 may be arranged on an operation panel 13 in addition to an ordinary start button 132. In this condition, when the refeed button 133 is pressed, the papers are refed, have their fiber orientations sensed, and driven out to the discharge tray 12 if indefinite in fiber orientation.

3rd Embodiment

A third embodiment will be described with reference also made to FIG. 12. The following description will concentrate on the difference between the second and third embodiments. In the second embodiment, after the fiber orientation of the paper 5 has been sensed, the paper 5 is reoriented, as needed. By contrast, in the third embodiment, the toner separating and paper drying unit 8 is operated in variable conditions matching the sensed fiber orientation of the paper 5. This insures the removal of the toner from the paper 5 without slowing down the removal, and frees the paper 5 from creases and tears and from defective image transfer when reused for image formation. Press rollers 86 are respectively pressed against the separator roller 82 and drier rollers 86 each accommodating a heater, not shown, therein. The paper 5 is conveyed by such roller pairs. The drier rollers 84 and press rollers 86 are provided in two pairs while a path selector 87 is interposed between the two roller pairs. The paper 5 is steered by the path selector 87 into a bypass 88 bypassing the rollers 84 and 86, as needed. Suitable conveyor roller pairs 89 are arranged on the transport path defined in the toner removing and paper drying unit 8.

Figure 13A:
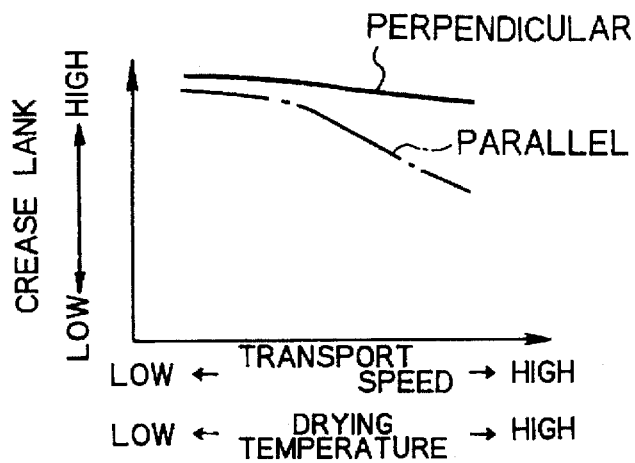
FIG. 13A shows a relation between the transport speed and drying temperature at a drying stage and the crease rank particular to the third embodiment.

When the fiber orientation of the paper 5 is substantially perpendicular to the direction of paper transport, the paper 5 creases little even when the transport speed is increased, as shown in FIG. 13A. Hence, this kind of paper 5 is dried by the drier rollers 84 and press rollers 86 at the usual speed, under the control of the control section. On the other hand, the paper 5 whose fiber orientation is substantially parallel to the direction of paper transport is apt to crease when the transport speed is high, as stated earlier. For this kind of paper, the rotation speed of the various rollers, i.e., the transport speed is lowered during the course of drying. However, the decrease in transport speed cause the paper 5 to be dried to an excessive degree. To obviated excessive drying, the path selector 87 is switched over to select the bypass 88. As a result, the paper 5 is conveyed along the bypass 88, bypassing the drier rollers 84 and press rollers 86 associated therewith.

As stated above, when the fiber orientation of the paper 5 is substantially parallel to the direction of paper transport, the transport speed is lowered during the course of drying so as to prevent the paper 5 from creasing. When the fiber orientation is substantially perpendicular to the above direction and causes the paper 5 to crease little, the paper 5 is dried at the usual transport speed. This prevents the transport speed for toner removal from being lowered. Further, when the transport speed is lowered, the paper 5 is driven into the bypass 88 in order to reduce the transport distance. As a result, the paper is free from excessive drying and insures desirable image transfer when reused for image formation. In addition, the paper 5 is allowed to bypass the drying station and more positively freed from creases.

Figure 13B:
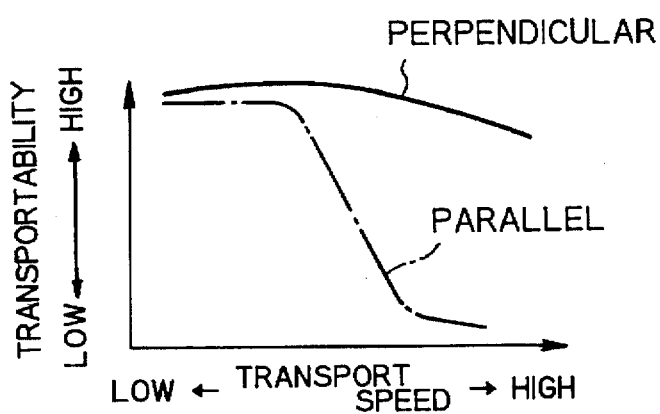
FIG. 13B shows a relation between the transport speed and the transportability at a liquid applying stage particular to the third embodiment.

In the above embodiment, for the paper 5 whose fiber orientation is substantially parallel to the direction of paper transport, the rotation speed of the various rollers is lowered so as to lower the transport speed during the course of drying. Alternatively, the heat to be applied from the drier roller 84 to the paper 5 may be reduced because this kind of scheme also causes the paper 5 to crease little, as shown in FIG. 13A. However, because reducing the heat of the drier roller 84 is apt to result in the short drying of the paper 5, it is preferable to increase the drying distance which the paper travels 5 or to combine the decrease in heat with the decrease in transport speed. Further, as shown in FIG. 13B, when the transport speed of the liquid applying unit 7 is high during the course of liquid application, the transportability is deteriorated, e.g., the paper 5 is torn. To solve this problem, there may be lowered the rotation speed of the rollers included in the liquid applying unit 7, i.e., the transport speed during the course of liquid application.

Figure 14:
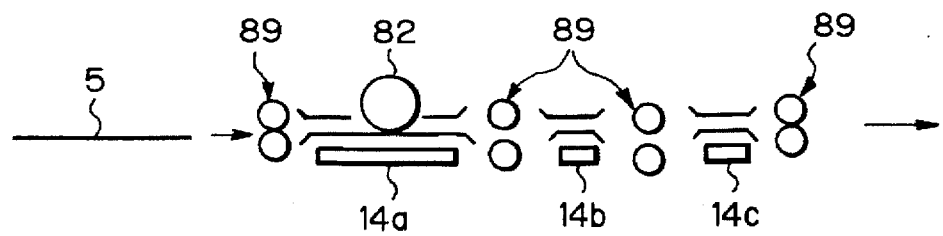
FIG. 14 shows a toner separating and paper drying unit representative of a modification of the third embodiment.

To change the distance which the paper 5 travels at the drying stage, the above embodiment uses the path selector 87 and bypass 88. FIG. 14 shows an alternative arrangement including three panel type heaters 14a, 14b and 14c. Among them, the downstream heaters 14b and 14c are used as drying means. For the paper 5 whose fiber orientation is substantially perpendicular to the direction of paper transport, the heaters 14b and 14c are both turned on. For the paper 5 whose fiber orientation is substantially parallel to the above direction, the most downstream heater 14c is turned off so as to reduce the drying distance.

Figure 15A:
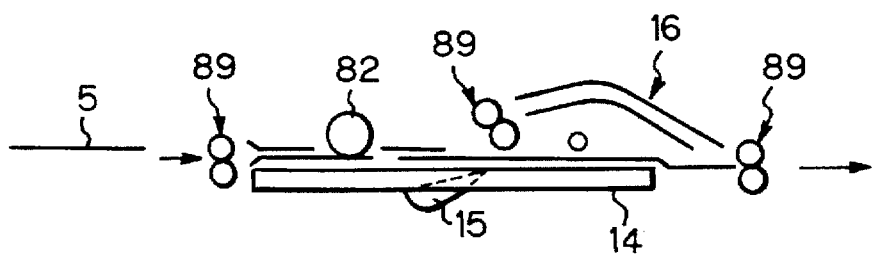
FIG. 15A shows a toner separating and paper drying unit representative of another modification of the third embodiment.
Figure 15B:
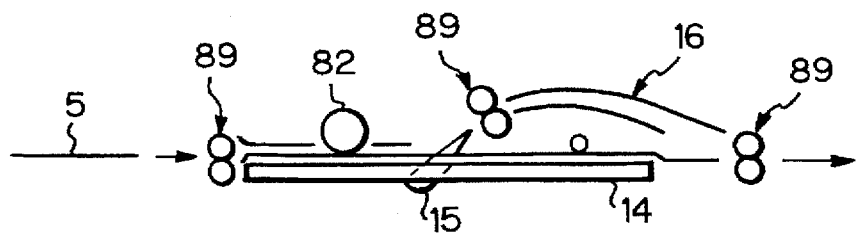
FIG. 15B demonstrates the operation of the modification shown in FIG. 15A.

Also, as shown in FIGS. 15A and 15B, use may be made of a single panel type heater 14 for heating the paper 5 throughout the toner removing stage and paper drying stage. A path selector 15 is positioned on the paper transport path at the center of the heater 14. When the fiber orientation of the paper 5 is substantially perpendicular to the direction of paper transport, the path selector 15 is so position as to cause the paper 5 to move over the entire surface of the heater 14, as shown in FIG. 15A. By contrast, for the paper 5 whose fiber orientation is substantially parallel to the direction of paper transport, the path selector 15 is so positioned as to steer the paper 5 into a bypass 16 at the intermediate portion of the heater 14. As a result, the distance which the paper 5 travels at the drying stage is reduced.

Figure 16A:
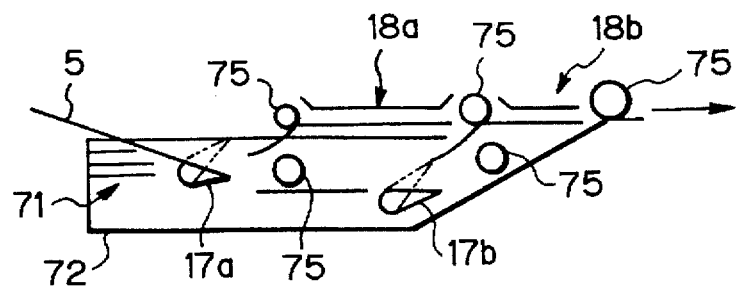
FIG. 16A shows a liquid applying unit representative of still another modification of the third embodiment.
Figure 16B:
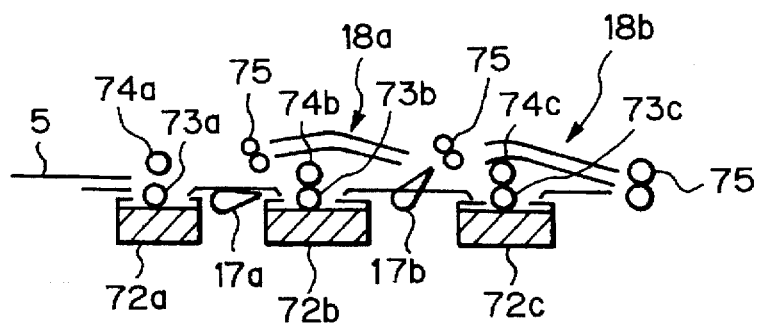
FIG. 16B demonstrates the operation of the modification shown in FIG. 16A.

As for the paper 5 whose fiber orientation is substantially parallel to the direction of paper transport, a decrease in the transport speed of the liquid applying unit 7 deteriorates the transportability, e.g., tears the paper 5, as shown in FIG. 13B. In light of this, there may be reduced the rotation speed of the rollers included in the unit 7, i.e., the transport speed during the course of liquid application. However, a decrease in the transport speed at the liquid applying stage results in an increase in the period of tome over which the paper 5 is wetted by the liquid 71. As a result, the paper 5 looses its elasticity and is apt to jam the path or crease. Therefore, it is preferable to reduce the distance which the paper 5 travels at the liquid applying stage, so that the paper 5 may be wetted in a substantially constant amount without regard to the transport speed. FIGS. 16A and 16B each shows a specific configuration for reducing the above distance. In FIG. 16A, two path selectors 17a and 17b are sequentially arranged on a transport path defined within the vessel 72, while bypasses 18a and 18b are defined above the vessel 72. The path selectors 17a and 17b selectively cause the paper 5 to move along the bypasses 18a and 18b or along the entire underwater path. In FIG. 16B, three liquid applying units are arranged in series and respectively have liquid vessels 72a, 72b and 72c and applicator rollers 73a, 73b and 73c. In this configuration, the path selectors 17a and 17b are controllably switched over to change the number of liquid applying units over which the paper 5 is to move, i.e., the distance which the paper 5 moves at the liquid applying stage.

4th Embodiment

Figure 17:
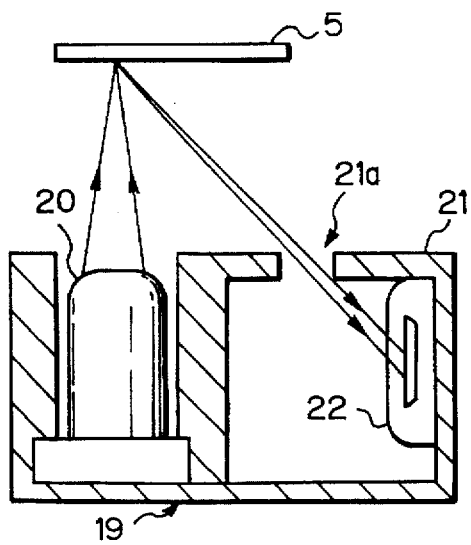
FIG. 17 is a section showing a thickness sensor included in a fourth embodiment of the present invention.

This embodiment is similar to the third embodiment except that the fiber orientation sensing unit 10 is replaced with a thickness sensor 19 shown in FIG. 17. While the thickness sensor 19 senses the thickness of the paper 5, the drying condition of the toner removing and paper drying unit 8 are varied on the basis of the output of the sensor 19. As shown in FIG. 17, the sensor 19 is an ultraminiature displacement sensor made up of an LED 20, a casing 21, and a position sensing device implemented as a PSD 22. When the LED 20 emits a convergent light toward the surface of the paper 5, the resulting reflection from the paper 5 is incident to the PSD 22 via a slit 21a formed in the casing 21 and forms a spot thereon.

When the distance between the paper 5 and the LED 20 is varied, the angle of the reflection incident to the PSD 22 via the slit 21a varies. As a result, the position of the beam spot on the light-sensitive surface of the PSD 22 is displaced. The distance between the LED 20 and the surface of the paper 5 can be determined in terms of the displacement of the beam spot from a reference position. Therefore, if the distance between the LED 20 and the surface which the paper 5 contacts during transport (reference surface) is measured beforehand, it is possible to calculate the thickness of the paper 5. Specifically the LED 20 emits a light having a wavelength of 940 nm and forming a spot of 1.3±0.2 mm at a measuring position. The distance between the measuring surface of the sensor 19 and the reference surface is 5 min. In these conditions, the sensor 19 is capable of measuring the displacement of the surface to be measured over a range of 5±1 mm, and has a resolution of ±10 μm.

Figure 18A:
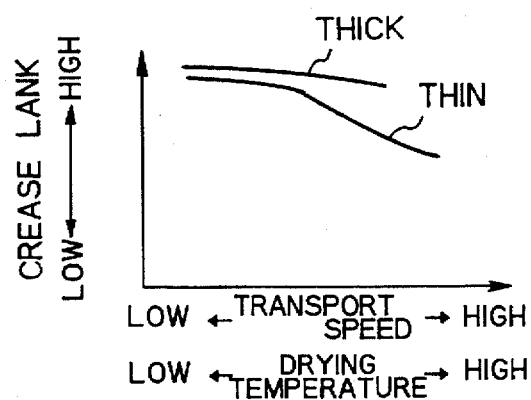
FIG. 18A shows a relation between the transport speed and drying temperature and the crease rank at a drying stage particular to the fourth embodiment.
Figure 19:
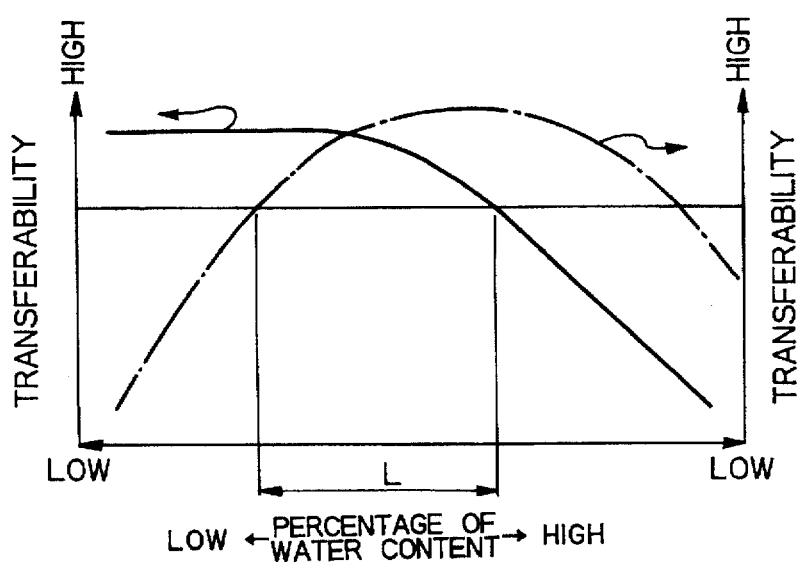
FIG. 19 shows a relation between the percentage of water content of a paper after toner removal and the portability and image transferability at the time of reuse and particular to the fourth embodiment.

In the illustrative embodiment, the paper 5 fed from the paper feeding unit 6 has its thickness measured by the sensor 19. As shown in FIG. 18A, when the sensed thickness is greater than a preselected thickness, the paper 5 creases little even even if the transport speed is increased. Hence, the control section, not shown, causes the drier rollers 84 and press rollers 86 to dry the paper 5 without lowering the transport speed, i.e., the toner removing speed. As also shown in FIG. 18A, when the thickness is smaller than the preselected thickness, the paper 5 is apt to crease if the transport speed is increased. For this kind of paper 5, the rotation speed of the rollers, i.e., the transport speed is lowered during the course of drying. However, as shown in FIG. 19, lowering the transport speed deteriorates the image transferability when the recycled paper 5 is reused for image formation. To solve this problem, the path selector 87 is actuated to steer the paper 5 into the bypass 88 bypassing the drier roller 84 and associated press roller 64. Labeled L in FIG. 19 is representative of an adequate range of the percentage of water content, i.e., (weight of paper—dry weight of paper)/dry weight of paper.

As stated above, when the paper 5 is thinner than a preselected thickness, the transport speed is lowered at the drying stage so as to free the paper 5 from creases. When the paper 5 is thicker than the preselected thickness and creases little, the usual transport speed is maintained at the drying stage which prevents the toner removal from being slowed down. When the transport speed is lowered, the paper 5 is driven into the bypass 88 in order to reduce the tran sport distance at the drying stage. This prevents the paper 5 from being excessively dried and thereby obviates defective image transfer when the recycled paper 5 is reused. At this instant, because the paper 5 bypasses the drying path, the probability of creasing is further reduced.

Figure 18B:
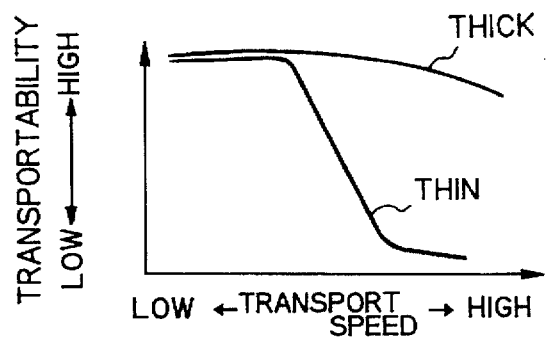
FIG. 18B shows a relation between the transport speed and the transportability at a liquid applying stage particular to the fourth embodiment.

As shown in FIG. 18A, even when the drying temperature is lowered, the above embodiment causes the paper 5 to crease little. Hence, the heating temperature of the drier roller 84 may be lowered in place of the transport speed, as in the third embodiment. Further, the drying section may be modified as shown in FIG. 14 or in FIGS. 15A and 15B in order to vary the transport distance at the drying stage. As shown in FIG. 18B, when the paper 5 is thicker than the preselected thickness, increasing the transport speed deteriorates the transportability, i.e., causes the paper 5 to crease easily. To solve this problem, the rotation speed of the rollers included in the liquid applying unit 7, i.e., the transport speed at the liquid applying stage may be lowered.

Figure 20:
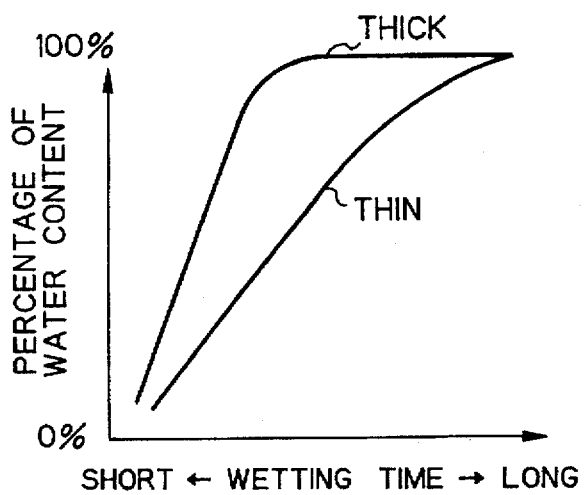
FIG. 20 shows a relation between the wetting time at the time of liquid application and the percentage of water content of the paper particular to the fourth embodiment.

When the transport speed is lowered at the liquid applying stage, as stated above, the wetting time (liquid applying time) increases to, in turn, increase the amount of liquid application to the paper 5, i.e., the amount of wetting of the paper 5. As a result, the paper 5 looses its flexibility and is apt to jam the path or to crease. In addition, as shown in FIG. 20, when the paper 5 is thin, an increase in wetting time results in a sharp increase in the amount of wetting. In light of this, it is preferable to reduce the distance which the paper 5 travels at the liquid applying stage, thereby maintaining the amount of wetting substantially constant without regard to the transport speed. For this purpose, the modification shown FIG. 16A or 16B may be used.

Figure 21:
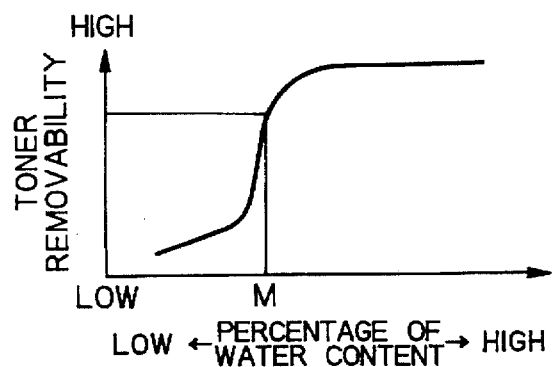
FIG. 21 shows a relation between the percentage of water content of the paper after liquid application and the toner removability particular to the fourth embodiment.

Moreover, as shown in FIG. 21, when the percentage of water content of the paper 5 decreases below a preselected value M, the removal of the toner is degraded. Hence, for the thick paper 5, it is preferable that the wetting time (transport speed×distance for liquid application) be increased to set up the preselected percentage of water content (M or above in FIG. 21).

In summary, the present invention achieves various unprecedented advantages as enumerated below.

(1) The fiber orientation of a paper can be accurately determined by a nondestructive non-contact system.

(2) Even when light emitting means is displaced along its optical axis, the density of a light incident to a paper varies little. This reduces the variation of the diffused reflection distribution of a reflection from the paper.

(3) The distance between the light emitting means and light sensing means can be reduced in order to implement a compact arrangement.

(4) The distance between the light emitting means and the light receiving means can be long enough to promote free layout.

(5) The fiber orientation of the paper can be easily determined because the intensity of the reflection noticeably changes with a change in fiber orientation.

(6) The diffused reflection distribution at a position substantially parallel to an optical axis plane and the distribution at a position substantially perpendicular to the same are compared. This allows a fiber orientation to be accurately determined even when the distribution changes due to a change in the kind of the paper.

(7) It is possible to reduce the noise level of the diffused reflection distribution.

(8) The accurate determination of a fiber orientation is enhanced because the difference due to the fiber orientation in the diffused reflection distribution is great.

(9) Even when the operator stacks the papers on first medium stacking means without being conscious of the fiber orientation, the papers are free from creases. When the fiber orientation of the paper is substantially perpendicular to the direction of paper transport, it is determined that the paper can be subjected to the removal of an image forming substance and using an unstabilizing liquid. Then, the paper is directly conveyed to liquid applying means. This prevents the processing speed from being lowered.

(10) The presence of the papers which cannot be subjected to toner removal on second medium stacking means is reported to the operator. Hence, the operator can pick up such papers from the second medium stacking means, rotate them substantially 90 degrees with respect to the direction of paper transport, and again stack them on the first medium stacking means. As a result, the papers can be processed with their fibers oriented substantially perpendicularly to the direction of paper transport.

(11) Even when the operator stacks the papers on the first medium stacking without being conscious of the fiber orientation, all the papers are free from creases.

(12) The fiber orientation of the rotated paper is again sensed by fiber orientation sensing means. If the sensed fiber orientation is indefinite and cannot be subjected to the removal of the image forming substance, the paper is driven out to third medium stacking means. Hence, this kind of paper can be dealt with independently of the other papers.

(13) When the fiber orientation of the paper is substantially parallel to the direction of paper transport, drying means is operated at a speed lower than a preselected speed or at a temperature lower than a preselected temperature, thereby preventing the paper from being sharply dried. Hence, even when the operator stacks the papers on the first medium stacking means without being conscious of the fiber orientation, all the papers are free from creases. Further, the drying means is operated over a distance smaller than a preselected distance so as to prevent the paper from being excessively dried. This insures desirable image transfer when the recycled paper is reused. When the fiber orientation of the paper is substantially perpendicular to the direction of paper transport, the drying means is operated at the preselected speed and temperature and over the preselected distance. As a result, the paper can be dried such that its percentage of water content lies in a preselected range. This prevents the processing speed from being lowered.

(14) When the fiber orientation of the paper is substantially parallel to the direction of paper transport, the liquid applying means is operated at a speed lower than a preselected speed so as not to apply the liquid sharply to the paper. Hence, even when the operator stacks the papers on the first medium stacking means without being conscious of the fiber orientation, all the papers are free from creases and tears. Because the liquid applying means is operated over a liquid applying distance smaller than a preselected distance, the percentage of liquid content of the paper is prevented from becoming excessively great. Hence, jams and creases ascribable to the decrease in the elasticity of the paper are obviated. When the fiber orientation of the paper is substantially perpendicular to the direction of paper transport, the liquid applying means is operated at the preselected transport speed and over the preselected distance. This provides the paper with the preselected percentage of liquid content and thereby prevents the processing speed from being lowered.

(15) When the thickness of the paper or image holding means is smaller than a preselected thickness, the drying means is operated at the transport speed lower than the preselected transport speed or at the temperature lower than the preselected temperature, thereby preventing the paper from being sharply dried. Hence, the paper is free from creases. Because the drying means is operated over the drying distance smaller than the preselected distance, the paper is prevented from being excessively dried. This insures desirable image transfer when the recycled paper is reused. When the thickness of the paper is greater than the preselected thickness, the drying means is operated at the preselected speed and temperature and over the preselected distance. As a result, the paper can be dried such that its percentage of liquid content lies in a preselected range. This prevents the processing speed from being lowered and prevents the transportability from being deteriorated when the paper is reused.

(16) When the thickness of the paper is smaller than the preselected thickness, the liquid applying means is operated at a speed lower than a preselected speed so as not to apply the liquid sharply to the paper. The paper is free from creases and tears. Because the liquid applying means is operated over the liquid applying distance smaller than the preselected distance, the percentage of liquid content of the paper is prevented from becoming excessively great. Hence, jams and creases ascribable to the decrease in the elasticity of the paper are obviated. When the thickness of the paper is greater than the preselected thickness, the liquid applying means is operated at the preselected transport speed and over the preselected dispreselected provides the paper with the preselected percentage of liquid content and thereby prevents the processing speed from being lowered while insuring the expected removal of the image forming substance.

Various modifications will become possible for those skilled in the art after receiving the teachings of the present disclosure without departing from the scope thereof.

What is claimed is:

1. An apparatus for removing an image forming substance from fibers constituting a surface of an image holding medium, said apparatus comprising:

first medium stacking means for stacking the image holding medium;

liquid applying means for applying to the image holding medium an unstabilizing liquid which unstabilizes adhesion between the image forming substance and the image holding medium;

fiber orientation sensing means for sensing an orientation of the fibers of the image holding medium conveyed from said first medium stacking means;

determining means for determining, based on the orientation sensed by said fiber orientation sensing means, whether or not the image holding medium can be subjected to a removal of the image forming substance and including an application of the unstabilizing liquid; and second medium stacking means for stacking the image holding medium which cannot be subjected to the removal, as determined by said determining means.

2. An apparatus as claimed in claim 1, further comprising one of audible alerting means and visible alerting means for informing an operator of a presence of the image holding medium which cannot be subjected to the removal on said second medium stacking means.

3. An apparatus as claimed in claim 1, further comprising rotating means for rotating the image holding means present on said second medium stacking means such that the image holding means is reoriented substantially 90 degrees with respect to an intended direction of medium transport, and then conveying the image holding medium to said liquid applying means.

4. An apparatus as claimed in claim 3, further comprising:

fiber orientation resensing means for again sensing the orientation after the image holding medium has been rotated by said rotating means;

redetermining means for again determining, based on the orientation sensed again, whether or not the image holding medium can be subjected to the removal of the image forming substance; and third medium stacking means for stacking the image holding medium which cannot be subjected to the removal, as determined by said redetermining means.

5. An apparatus for removing an image forming substance from fibers constituting a surface of an image holding medium, said apparatus comprising:

first medium stacking means for stacking the image holding medium;

liquid applying means for applying to the image holding medium an unstabilizing liquid which unstabilizes adhesion between the image forming substance and the image holding medium;

fiber orientation sensing means for sensing an orientation of the fibers of the image holding medium conveyed from said first medium stacking means;

determining means for determining, based on the orientation sensed by said fiber orientation sensing means, whether or not the image holding medium can be subjected to a removal of the image forming substance and including an application of said unstabilizing liquid; and rotating means for rotating the image holding medium which cannot be subjected to the removal of the image forming substance, as determined by said determining means, such that the image holding medium is reoriented substantially 90 degrees with respect to an intended direction of medium transport.

6. An apparatus as claimed in claim 5, further comprising:

fiber orientation resensing means for again sensing the orientation after the image holding medium has been rotated by said rotating means;

redetermining means for again determining, based on the orientation sensed again, whether or not the image holding medium can be subjected to the removal of the image forming substance; and third medium stacking means for stacking the image holding medium which cannot be subjected to the removal, as determined by said redetermining means.

7. An apparatus for removing an image forming substance from fibers constituting a surface of an image holding medium, said apparatus comprising:

liquid applying means for applying to the image holding medium an unstabilizing liquid which unstabilizes adhesion between the image forming substance and the image holding medium;

separating means for separating the image forming substance from the image holding medium to which the unstabilizing liquid has been applied;

drying means for drying the image holding medium from which the image forming substance has been removed;

fiber orientation sensing means for sensing an orientation of the fibers of the image holding medium; and control means for varying a drying condition of said drying means on the basis of the orientation sensed.

8. An apparatus for removing an image forming substance from fibers constituting a surface of an image holding medium, said apparatus comprising:

liquid applying means for applying to the image holding medium an unstabilizing liquid which unstabilizes adhesion between the image forming substance and the image holding medium;

fiber orientation sensing means for sensing an orientation of the fibers of the image holding medium; and control means for varying a liquid applying condition of said liquid applying means on the basis of the orientation sensed.

9. An apparatus for removing an image forming substance from fibers constituting a surface of an image holding medium, said apparatus comprising:

liquid applying means for applying to the image holding medium an unstabilizing liquid which unstabilizes adhesion between the image forming substance and the image holding medium;

separating means for separating the image forming substance from the image holding medium to which the unstabilizing liquid has been applied;

drying means for drying the image holding medium from which the image forming substance has been removed;

thickness sensing means for sensing a thickness of the image holding medium; and control means for varying a drying condition of said drying means on the basis of the thickness sensed.

10. An apparatus for removing an image forming substance from fibers constituting a surface of an image holding medium, said apparatus comprising:

liquid applying means for applying to the image holding medium an unstabilizing liquid which unstabilizes adhesion between the image forming substance and the image holding medium;

thickness sensing means for sensing a thickness of the image holding medium; and control means for varying a liquid applying condition of said liquid applying means on the basis of the thickness sensed.

* * * * *